United States Patent [19]
Jurecic et al.

[11] 4,343,418
[45] Aug. 10, 1982

[54] DISPENSER FOR DENTAL SEALANT

[75] Inventors: Anton Jurecic, Springfield; James V. Romano, Skippack Township, Montgomery County, both of Pa.

[73] Assignee: Pennwalt Corporation, Philadelphia, Pa.

[21] Appl. No.: 156,840

[22] Filed: Jun. 5, 1980

[51] Int. Cl.³ .............................................. G01N 1/14
[52] U.S. Cl. ................................. 222/386; 73/864.14
[58] Field of Search ............................. 222/386, 471; 73/864.14; 128/260, 261, 234; 32/40 A

[56] References Cited
U.S. PATENT DOCUMENTS 3,853,012  12/1974  Scordato et al. ............... 73/864.14
3,945,254   3/1976  Rebold .......................... 73/864.14
4,257,267   3/1981  Parsons ......................... 73/864.14

FOREIGN PATENT DOCUMENTS 717408  10/1931  France ............................ 128/234

Primary Examiner—Stanley H. Tollberg
Attorney, Agent, or Firm—Arthur M. Suga

[57] ABSTRACT

Device for dispensing liquids wherein a discardable tip of a dispenser is instantaneously automatically ejected upon application of slightly excessive thumb pressure to a member of the dispenser which, when normal thumb pressures are applied thereto, causes the liquid to be controllably dispensed through said tip onto a target such as a dentition surface.

9 Claims, 2 Drawing Figures

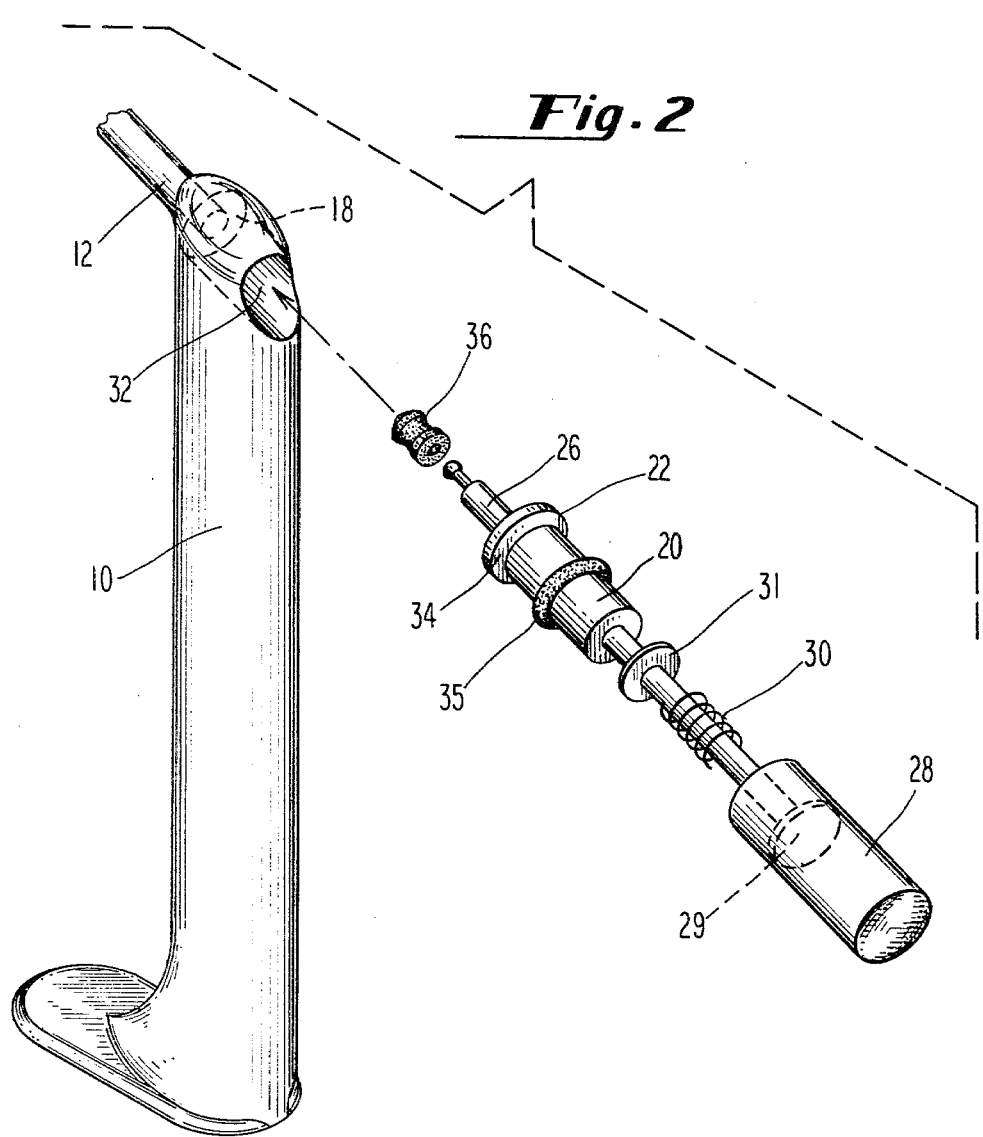

DISPENSER FOR DENTAL SEALANT

STATEMENT OF THE INVENTION

This invention relates to a liquid dispenser, and more particularly to a dispenser for dental sealants wherein a discardable dispensing tip of the dispenser may be automatically instantaneously ejected without the need for its manual separation.

BACKGROUND AND SUMMARY OF THE INVENTION

Dental pit and fissure sealants may be applied by any one of several types of applicators, such as brushes, sponges, cotton plegets with tweezers, dispensers with disposable tips made of plastic tubing, and the like. Each type applicator offers certain advantages depending upon the nature of the sealant being applied, and the dexterity of the operator.

Most dental pit and fissure sealants are liquids of varying viscosities. Some are polymerized by radiation from an ultraviolet light source while others are designed to be polymerized by high intensity visible light. Still others are polymerizable or set by means of a redox reaction between an organic peroxide and a reducing agent, commonly benzoyl peroxide with dimethyl-p-toluidine, and other tertiary amine derivaties of toluidine.

Application of the sealant by means of a brush is not entirely satisfactory. Only a small amount of the sealant is carried by the brush resulting in a time-consuming procedure with concomitant fatigue to the operator. Further, brushing the sealant onto surfaces of posterior teeth uniformly is difficult, and even skilled technicians accidentally misapply the sealant to soft tissue where it may cause irritation.

Plastic sponges and cotton plegets suffer from several disadvantages. Both are picked from a small box with tweezers. Very frequently, the sponges will cling together due to static electrical charges thereon. Similarly, intermingled fibrils of the cotton plegets will cause undesirable clinging. Both the plastic sponges and cotton plegets soak up large quantities of the sealant which tend to adhere quite tenaciously to the sponges and plegets. Cotton plegets frequently leave linters embedded in the sealant on the tooth surfaces where they often act as wicks to thus contribute to clinical failure. After each application, the sponge or pleget must be removed by hand from the tip of the tweezers. In multiple applications of sealant in the mass treatment of school children, for example, sealant accumulates on the tweezers to further add to the frustrations of the operator.

Sealants may also be applied by means of a dispenser. A small tube or tip of plastic is inserted into the dispenser head. A lever, mounted behind the head of the dispenser, is depressed to actuate a rubber diaphragm for expelling a small amount of air therewithin. Releasing the lever while the end of the dispensing tip is immersed in the sealant urges some into the tip where it may then be applied to the oral cavity by again depressing the lever. Such dispensing devices are not entirely satisfactory. For example, the head of many prior art dispensers is relatively bulky, and when placed inside an oral cavity, often obstructs clear vision of the dentition, especially in the smaller cavities of children. Also contributing to obstructed vision is the clinical operator's own hand which depresses the lever.

Further, the disposable plastic tip is seated in the head of the dispenser rather loosely. Consequently, it is often difficult to avoid the flow of sealant into the rubber diaphragm, and particularly where the end of the plastic tip is directed upwardly, as when sealant is applied to maxillary dentition. After the sealant is applied, the plastic tip must be manually removed from the dispenser, subjecting the operator to contact with the sealant necessitating time-consuming and annoying removals thereof.

The present invention substantially overcomes the deficiencies of prior art applicators or dispensers and permits a precise amount of sealant to be applied to dentition of the maxilla or mandible. After the sealant has been applied, the tip is instantaneously ejected upon the mere application of slightly excessive pressure to a plunger member which, under normal operating thumb pressures, will urge the sealant from the dispenser onto the dentition surfaces. The ability of the present dispensing device to thus eject the disposable tip without manually unscrewing or physically separating it from the dispenser is an important feature of the invention contributing to its safe, aseptic, and convenient usage.

The present dispenser may be used to apply sealant to a single tooth surface, estimated to require between about 2 to 6 mg; or to an entire quadrant, since the dispenser is capable of carrying more than 50 mg of the sealant. The combined length of the tip with approximately one-half the syringe body makes it convenient for the operator to apply the sealant to posterior teeth without visual obstruction by the head of the dispenser or by the operator's hand. The handle is comfortably held and can be rotated to any desirable position.

BRIEF DESCRIPTION OF THE DRAWINGS

FIG. 2 is a partially exploded perspective view of the dispenser illustrated in FIG. 1.

DETAILED DESCRIPTION OF THE DRAWINGS

Figure 1:
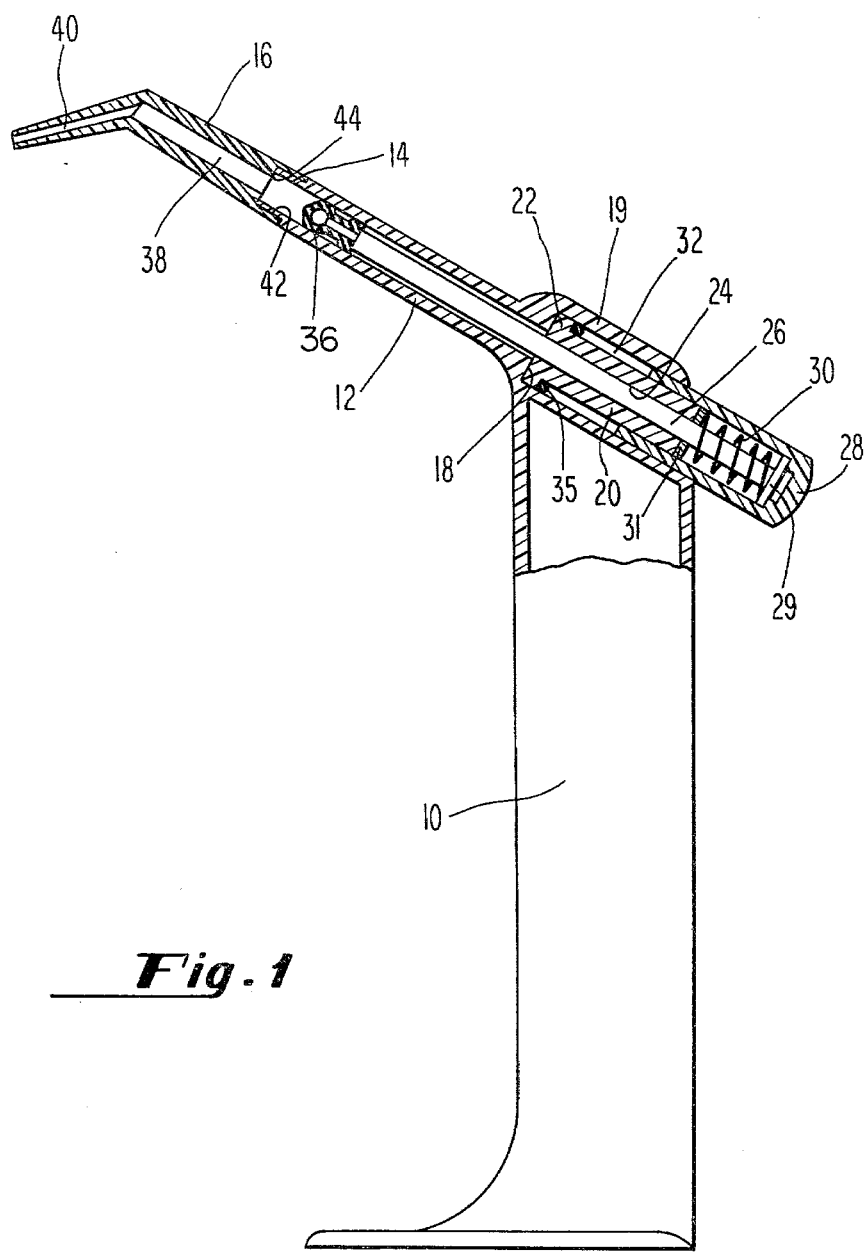
FIG. 1 is a longitudinal sectional view of the dispenser of the present invention.

The pit and fissure dispenser includes a handle 10, preferably elliptical in cross-section for ease of grasping and manipulation, and may be molded from a suitable plastic material integral with barrel 12. Barrel 12 is obliquely disposed to handle 10 and terminates in a tapered end portion 14 around which taper 14 a disposable and ejectable dispensing tip 16 is frictionally engaged. Barrel 12 is provided with a shoulder 18 adjacent a flared portion 19 at the rear of the barrel. A bushing 20 is tightly secured against shoulder 18 by means of bushing head 22 force fitted thereagainst within flared portion 19. Bushing 20 is provided with an axial bore 24. A plunger 26 is reciprocable within bore 24 and barrel 12 by means of an actuating cylinder or button 28 which is depressed by thumb pressure exerted thereagainst to thereby overcome the force exerted by compression spring 30, disposed around a rear portion of plunger 26 and interposed between bushing 20 and actuating button 28, or, if a washer 31 is employed, between it and the button 28. Plunger 26 may be integrally molded with button 28, or, as illustrated, molded with a disc 29 snugly received within button 28.

Actuating button 28 is slidably received within a cylindrical space 32 provided around bushing 20, the head 22 thereof forming a shoulder 34 against which a sealing O-ring 35 may be disposed, which O-ring also limits the forward movement of button 28. Of course, absent O-ring 35, forward movement of button 28, and hence plunger 26, is limited by shoulder 34.

A resilient sealing cap 36 is attached to the forward end of plunger 26, the cap 36 being snugly received within barrel 12 and frictionally slidable therewithin.

Dispensing tip 16 is not straight, but angled as shown, in order to facilitate easy access to posterior teeth, and includes a liquid sealant storage chamber 38 communicating with dispensing tip bore 40, and a tapered rear portion 42 configured to mate or complement barrel taper 14 to provide a reasonably secure frictional engagement therebetween. Taper 42 originates at a shoulder 44 of dispensing tip 16 which also defines the opening of chamber 38.

In operation, thumb pressure is applied to actuating button 28 to compress spring 30 to permit plunger 26 to move forwardly through bore 24, and both plunger 26 and cap 36 through barrel 12 to thereby force air out of dispensing tip 16. Cap 36 will not pass through bore 24. Forward movement of plunger 26 and cap 36 ceases when cap 36, of larger diameter than storage chamber 38, abuts shoulder 44 of dispensing tip 16. With plunger 26 and cap 36 thus in a substantially full forward position, tip of dispensing tip 16 is immersed in the sealant liquid. Release of thumb pressure on button 28 allows spring 30 to urge button 28 to its original at-rest position, creating a partial vacuum inside tip 16 which draws sealant into chamber 38, the diameter of which is sufficiently small such that capillary action prevents the sealant liquid therein from entering barrel 12 regardless of orientation of dispensing tip 16. Further, spring 30 is of a designed stiffness to assure that a predictable amount of sealant is drawn into the dispensing tip after button 28 is released. Sealant may now be applied to the target surface within the patient's mouth by again applying gentle thumb pressure to button 28. Dispensing tip 16 may be manually rotated about the longitudinal axis of barrel 12 by overcoming the frictional engagement between tapers 14 and 42.

Frictional engagement between tapers 14 and 42 is not overcome when sealant is being dispensed onto a target surface. However, when tip 16 is desired to be ejected, by merely exerting slightly excessive, or sudden pressure on button 28, cap 36 will impact shoulder 44 with sufficient force to overcome the frictional resistance between tapers 14 and 42 to instantaneously eject the dispensing tip, thus contributing to the speed, cleanliness, and efficiency of the sealant dispensing operation.

Shoulder 34 of bushing 20, or O-ring 35, limits forward movement of button 28, and hence plunger 26 and cap 36, to preclude any possibility of cap 36 completely exiting barrel 12.

It is not intended that the present device be limited in its application to a pit and fissure sealant. The device could readily administer dental glazes, cavity liners, luting cements, cervical coatings, and the like, and other medications or restorative materials. For example, the present dispenser may be used advantageously in the oral administration of medicines or testing substances to small animals; applications of adhesives to confined areas, narrow lines, etc.

Since the dispensing tip can be designed to other suitable sizes and shapes depending upon the intended application, i.e., industrial, home, school, office, etc., it is apparent that the invention may be practiced other than as described herein.

Suitable plastic materials for the dispenser, other than metallic spring 30 and washer 31, O-ring 34 and cap 36, may be polyvinyl chloride, polyethylene, polypropylene, polyamide, polyacetal, acrylonitrile-butadiene-styrene, and the like.

I claim:

1. A dispenser for the controlled delivery of a liquid contained therewithin comprising
   a dispenser handle,
   a barrel arranged in operable disposition with said handle, said barrel having a rearwardly disposed flared portion,
   a plunger arranged for reciprocable movement within said barrel,
   a bushing fitted against said flared portion and in alignment therewith, said bushing having a head at a forward portion thereof of larger diameter then remainder of said bushing, said bushing head forcefitted against a forward portion of said flared portion of said barrel, said bushing and bushing head having an axial bore therethrough for receiving said plunger reciprocably therein,
   a dispensing tip communicating with and frictionally engaged to a forward portion of said barrel,
   means for imparting said reciprocable movement to said plunger whereby said liquid is controllably dispensed through said dispensing tip upon application of a dispensing pressure to said plunger, said plunger ejecting said dispensing tip from said forward portion of said barrel upon application to said plunger of a pressure excessive of said dispensing pressure.

2. The dispenser of claim 1 wherein said handle is elliptical in cross-section.

3. The dispenser of claim 1 wherein said barrel and handle form an integral mold and are disposed obliquely to each other.

4. The dispenser of claim 1 further characterized by said barrel flared portion and bushing providing a confined cylindrical space therebetween,
   said means comprising a cylindrical actuating button adapted for reciprocable movement within said space whereby pressure exerted against said button produces forward movement thereof within said space to cause said plunger to similarly move forward through said bushing bore and barrel.

5. The dispenser of claim 4 wherein one end of said plunger is secured within said button to a rearward portion thereof, and said means further comprises
   a spring within said button disposed about said plunger at a most rearward portion thereof to urge said button in a rearward direction after said dispensing pressure is released therefrom to thereby cause said plunger and button to move rearwardly.

6. The dispenser of claim 5 wherein said dispensing tip includes a liquid storage chamber towards a rear portion thereof.

7. The dispenser of claim 6 wherein said dispensing tip is frictionally engaged to said forward portion of said barrel by respective complementary tapers, said taper of said dispensing tip terminating in a shoulder wherein said liquid storage chamber commences.

8. The dispenser of claim 7 wherein a resilient sealing cap is removably affixed to a forwardmost tip of said plunger.

9. The dispenser of claim 8 wherein said cap impacts said dispensing tip shoulder to eject said dispensing tip from said barrel when said excessive pressure is applied to said plunger through said button.

* * * * *